United States Patent
Koblenski et al.

(10) Patent No.: US 11,071,836 B2
(45) Date of Patent: Jul. 27, 2021

(54) SINGLE DOSE INHALER MONITORING ATTACHMENT

(71) Applicant: Reciprocal Labs Corporation, Madison, WI (US)

(72) Inventors: Samuel A. Koblenski, Madison, WI (US); Gregory F. Tracy, Madison, WI (US); David Hubanks, Madison, WI (US); Amber Michelle Markey, Madison, WI (US); Benjamin J. Kopp, Verona, WI (US); Justin Conrad Krosschell, Sioux Falls, SD (US); Leah J. Morrell, Madison, WI (US)

(73) Assignee: Reciprocal Labs Corporation, Madison, WI (US)

( * ) Notice: Subject to any disclaimer, the term of this patent is extended or adjusted under 35 U.S.C. 154(b) by 455 days.

(21) Appl. No.: 15/940,952

(22) Filed: Mar. 29, 2018

(65) Prior Publication Data
US 2019/0298942 A1    Oct. 3, 2019

(51) Int. Cl.
*A61M 15/00* (2006.01)
*G16H 20/13* (2018.01)
(Continued)

(52) U.S. Cl.
CPC .......... *A61M 15/008* (2014.02); *A61B 7/003* (2013.01); *G06M 1/026* (2013.01); *G16H 10/60* (2018.01);
(Continued)

(58) Field of Classification Search
None
See application file for complete search history.

(56) References Cited

U.S. PATENT DOCUMENTS

| 5,331,953 | A | | 7/1994 | Andersson et al. |
| 5,505,195 | A | * | 4/1996 | Wolf ................. A61M 15/0045 128/200.23 |

(Continued)

FOREIGN PATENT DOCUMENTS

| EP | 3471806 A1 | 4/2019 |
| WO | WO 2015/178907 A1 | 11/2015 |

(Continued)

OTHER PUBLICATIONS https://www.thomasnet.com/articles/instruments-controls/limit-switches/; Nov. 5, 2020.*
(Continued)

*Primary Examiner* — Bradley H Philips
(74) *Attorney, Agent, or Firm* — Fenwick & West LLP

(57) ABSTRACT

A medicament device sensor (Sensor) comprises a body, a front wall, a back wall, an audio sensor, and a plurality of pressure sensors. The body includes a bottom surface on which the various sensors are coupled. The front wall and the back wall provide mirror symmetry in at most one plane, thereby defining a single orientation in which the Sensor attaches to the medicament device. The front wall includes a securement clip that attaches to a ledge on the medicament device. To detect secure attachment of the Sensor to the medicament device, one pressure sensor detects pressure when the Sensor is secured to the medicament device. Another one or more pressure sensors detect depression of one or more dosing buttons confirming priming of the medicament device. The audio sensor detects an inhalation confirming dispensing of medicament. In effect, the Sensor determines a dispensing event has occurred.

20 Claims, 8 Drawing Sheets

(51) Int. Cl.
    *G16H 10/60*    (2018.01)
    *A61B 7/00*     (2006.01)
    *G06M 1/02*     (2006.01)
    *A61M 16/00*    (2006.01)
    *A61B 5/11*     (2006.01)
    *G16H 50/30*    (2018.01)
    *A61B 5/00*     (2006.01)

(52) U.S. Cl.
    CPC ............ *G16H 20/13* (2018.01); *A61B 5/1112* (2013.01); *A61B 5/4833* (2013.01); *A61B 2560/028* (2013.01); *A61M 15/0001* (2014.02); *A61M 15/003* (2014.02); *A61M 15/009* (2013.01); *A61M 15/0035* (2014.02); *A61M 15/0041* (2014.02); *A61M 2016/0018* (2013.01); *A61M 2016/0021* (2013.01); *A61M 2202/064* (2013.01); *A61M 2205/14* (2013.01); *A61M 2205/332* (2013.01); *A61M 2205/3375* (2013.01); *A61M 2205/3553* (2013.01); *A61M 2205/3569* (2013.01); *A61M 2205/3576* (2013.01); *A61M 2205/3584* (2013.01); *A61M 2205/3592* (2013.01); *A61M 2205/505* (2013.01); *A61M 2205/52* (2013.01); *G16H 50/30* (2018.01)

(56) References Cited

U.S. PATENT DOCUMENTS

| | | | |
|---|---|---|---|
| 8,807,131 | B1 | 8/2014 | Tunnell et al. |
| 9,352,107 | B2 | 5/2016 | von Hollen et al. |
| 9,555,200 | B2 | 1/2017 | Hosemann et al. |
| 9,782,550 | B2 | 10/2017 | Morrison et al. |
| 9,821,127 | B2* | 11/2017 | Barber .................. A61M 15/08 |
| 2010/0192948 | A1 | 8/2010 | Sutherland et al. |
| 2013/0151162 | A1* | 6/2013 | Harris ............... A61M 15/0021 702/19 |
| 2014/0182584 | A1 | 7/2014 | Sutherland et al. |
| 2014/0263455 | A1* | 9/2014 | Keenan ............. A61M 15/0026 222/153.13 |
| 2016/0144141 | A1 | 5/2016 | Biswas et al. |
| 2016/0228657 | A1 | 8/2016 | Sutherland |
| 2016/0325058 | A1* | 11/2016 | Samson ................. A61B 5/087 |
| 2017/0246406 | A1* | 8/2017 | Sutherland ........ A61M 15/0086 |
| 2017/0290527 | A1 | 10/2017 | Morrison et al. |
| 2018/0264207 | A1 | 9/2018 | von Hollen et al. |
| 2019/0105450 | A1 | 4/2019 | Sutherland et al. |

FOREIGN PATENT DOCUMENTS

| | | |
|---|---|---|
| WO | WO 2016/111633 A1 | 7/2016 |
| WO | WO 2017025642 A2 | 2/2017 |
| WO | WO 2017/141194 A1 | 8/2017 |
| WO | WO2018/160073 A1 | 9/2018 |
| WO | WO 2019/021254 A1 | 1/2019 |

OTHER PUBLICATIONS

PCT International Search Report and Written Opinion, PCT Application No. PCT/US2019/024524, dated Jul. 8, 2019, 13 pages.

* cited by examiner

SINGLE DOSE INHALER MONITORING ATTACHMENT

BACKGROUND

Field of Art

The disclosure relates generally to a medicament inhalation device monitoring attachment.

Description of the Related Art

Asthma remains a significant and costly public health problem. Worldwide, the World Health Organization estimates the population with asthma may be 300 million, and predicts that it will rise to 400 million by 2025. In the United States, asthma affects 1 in 12 individuals in the U.S. and prevalence is on the rise, leading to more than $56 billion per year in health care utilization costs.

Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments; however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used.

More generally, medicament devices such as inhalers dispense corticosteroids which allow patients to manage respiratory symptoms such as constricted airflow. When patients use medicament devices, the ability to accurately record instances of medication events and send recorded instances to physicians allows better monitoring of patients by physicians. A medicament device sensor attached to such medicament devices such as inhalers can aid in recording instances of medicament dispensing and transmitting the recorded instances to a server; however such events are generally reported much later than their time of occurrence, if at all. In some instances, such events are reported many hours if not days later, which is problematic.

SUMMARY

The present disclosure describes a medicament device sensor, specifically a single dose inhaler monitoring attachment. The single dose inhaler is used to provide a single medicament dose at a time through priming of the medicament dose then inhalation by a user. The monitoring attachment has many features which aim to secure the monitoring attachment to the single dose inhaler. These features include a securement clip, a body including two walls with asymmetry, and grooves corresponding to dosing buttons on the single dose inhaler. The securement clip fits over a ledge on the single dose inhaler. The body is asymmetrically shaped in at least two orthogonal planes such that there is one orientation for securing the monitoring attachment onto the single dose inhaler. The body also comprises a wall opposite that of the securement clip which provides tension on the single dose inhaler. The grooves along either side of the monitoring attachment allow for the single dose inhaler's dosing buttons to fit in the grooves. To detect whether the monitoring attachment is secured to the single dose inhaler, the monitoring attachment uses a limit switch that is depressed when the monitoring attachment is firmly secured onto the single dose inhaler. Once the monitoring attachment is secured, the monitoring attachment can activate other sensors for recording medicament usage events.

For accurately recording priming of the medicament dose and inhalation by the user, the monitoring attachment comprises two limit switches coupled to the dosing buttons and an audio sensor. The two limit switches are depressed when the two dosing buttons on the single dose inhaler are pressed. If a capsule with the medicament dose is loaded into the single dose inhaler, pressing the two dosing buttons punctures the capsule. After a capsule is punctured, the capsule spins around prior to inhalation of the medicament by a user. The audio sensor detects audio signals for both the spinning of the capsule and the inhalation by the user. For recording an instance of the medicament event, the monitoring attachment awaits confirmation from the limit switches and from the audio sensor.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
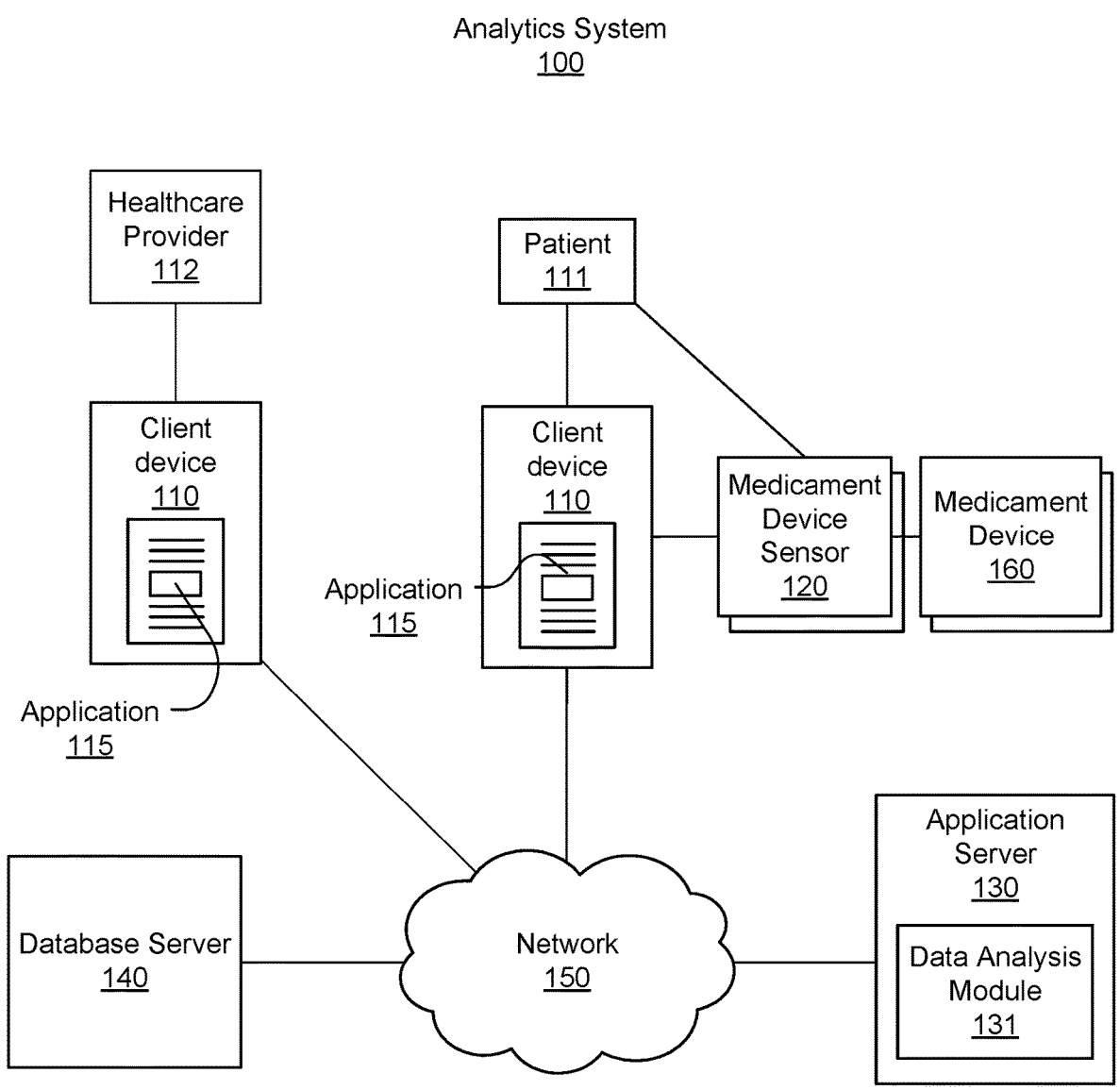
FIG. 1 shows an analytics system for monitoring accurate, real-time medicament device usage, performing analytics on that data, and providing notifications around medicament device events, according to one embodiment.

FIG. 1 shows an analytics system 100 for monitoring accurate, real-time medicament device usage, performing analytics on that data, and providing information about those events, according to one embodiment.

The analytics system includes client computing devices 110 (herein referred to as simply "client 110"), a medicament device sensor 120 (herein referred to as simply "sensor 120"), a medicament device 160, an application server 130, a database server 140, and a network 150. Although FIG. 1 illustrates only a single instance of most of the components of the analytics system 100, in practice more than one of each component may be present, and additional or fewer components may be used in conjunction with the components shown.

I.A. Client and Application

The clients 110, at the behest of their users, interact with the analytics system 100 via the network 150. For purposes of explanation and clarity it is useful to identify at least two different types of users. A patient 111 is a user burdened with a medical challenge who makes use of the analytics system 100 at least in part to obtain personalized risk notifications provided by the server 130 based on records by the sensor 120. Records recorded by the sensor 120 may include rescue and controller events involving rescue and controller medicament dispensing, respectively, by one or more medicament devices 160 (e.g., one for each type of medication). Such notifications can be provided in exchange for the user's permission to allow the analytics system 100 to monitor the patient's 111 medicament device 160 usage. As will be explained below, medication events are detected by a sensor 120 associated with the medicament device 160 and the user's client 110, which in turn reports to the application server 130, which in turn can initiate a process to generate notifications on the user's medical status as determined by the analytics system 100 which may be provided to the user through the client 110.

Another type of user is a healthcare provider 112 who, again with the patient's 111 express permission, also receives notifications regarding a patient's medicament management. In certain cases, the medicament device is a medical dose inhaler for providing medication, with some medication used for controlling asthma, chronic obstructive pulmonary disease, chronic sinusitis, allergies, another breathing challenge, etc. The patient 111 may also express permission for notifications to be shared with a community revolving around medicament usage event data and derived statistics regarding rescue events associated with medicament dispensing and other associated data. Other types of users are also contemplated, such as parents/guardians of patients 111 who may also want to receive notifications in the event that their own clients 110 are distinct from that of their children.

The client 110 is a computer system. An example physical implementation is described more completely below with respect to FIG. 2. The client 110 is configured to wirelessly communicate with the analytics system 100 via network 150. With network 150 access, the client 110 transmits to the analytics system 100 the user's geographical location and the time of a rescue medication event, as well as information describing the event as received from the associated sensor 120.

Regarding user location and event times, the client 110 may determine the geographical location and time of a rescue event through use of information about the cellular or wireless network 150 to which it is connected. For example, the current geographical location of the client 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client's 110 native operating system.

In addition to communicating with the application server 130, clients 110 connected wirelessly to the analytics system 100 may also exchange information with other connected clients 110. For example, through a client software application 115, a healthcare provider 112 may receive a notification describing a recent rescue event about a patient 111, then in response send a recommendation to the patient 111 for post rescue event treatment. Similarly, through application 115 patients 111 may communicate with their healthcare providers 112 and other patients 111.

Application 115 provides a user interface (herein referred to as a "dashboard") that is displayed on a screen of the client 110 and allows a user to input commands to control the operation of the application 115. The dashboard is the mechanism by which healthcare providers 112 and patients 111 access the analytics system 100. For example, the dashboard allows patients 111 and providers 112 to interact with each other, receive rescue event risk notifications, exchange messages about treatment, provide and receive additional event and non-event data, and so on. Application 115 may be coded as a web page, series of web pages, or content otherwise coded to render within an internet browser. Application 115 may also be coded as a proprietary software program configured to operate on the native operating system of the client 110. The dashboard is more completely described below in conjunction with FIG. 3.

In addition to providing the dashboard, application 115 may also perform some data processing on rescue event data locally using the resources of client 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client 110 have been paired with each other using a BTLE passkey, the sensor 120 automatically synchronizes and communicates information relating to medicament device 160 usage to the client 110. If the sensor 120 hasn't been paired with a client 110 prior to a rescue medication event, the information is stored locally until such a pairing occurs. Upon pairing, the sensor 120 communicates any stored event records to the client 110. In other implementations, other types of wireless connections are used (e.g., infrared or 802.11).

Although clients 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client 110. For example, a medicament device 160 may include an audiovisual interface including a display or other lighting elements as well as speakers for presenting visual audible information. In such an implementation the medicament device 160 itself may present the contents of notifications provided by the server 130 directly, in place of or in addition to presenting them through the clients 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers include a pressured propellant canister of aerosol medicine, a metering valve for delivering a regulated medicine dispensing amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament device 160. The sensor 120 is either removeably attachable to the medicament device without impeding the operation of the medication dispenser, or the sensor 120 is an integrated component that is a native part of the medicament device 160 as made available by its manufacturer.

The sensor 120 includes its own network adapter (not shown) that communicates with the client 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client 110 in every exchange of data. These two methods of communicating are not mutually exclusive, and the sensor 120 may be configured to communicate with both the client 110 and the application server 130, for example using redundant transmission to ensure event data arrives at the application server 130 or to provide information directly to the client 110 while the application server 130 is determining what notification to provide in response to an event.

As introduced above, the sensor 120 captures data about usage of the medicament device 160. Specifically, each sensor 120 captures the time and geographical location of the rescue medication event, that is, usages of the rescue medicament device 160, by the patient 111. Each sensor 120 transmits the event data in real-time or as soon as a wireless connection is achieved, automatically without input from the patient 111 or health care provider 112. The medication event information is sent to the application server 130 for use in analysis, generation of rescue event notifications, and in aggregate analyses of event data across multiple patients.

To accomplish this goal, there are a number of different ways for the sensor 120 to be constructed, and in part the construction will depend upon the construction of the medicament device 160. Generally, all sensors 120 will include an onboard processor, persistent memory, and the network adapter mentioned above that together function to record, store, and report medication event information to the client 110 and/or server 130. Sensors 120 may also include a clock for recording the time and date of events and/or a Global Positioning System (GPS) receiver for recording GPS coordinates of the sensors 120.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry that may report event information as an electrical data signal which a sensor 120 is designed to receive and interpret, for example the medicament device 160 itself may report movement, priming, and activation to the sensor 120.

The sensor 120 may store parameters incorporated for use with recording medicament dispensing events by the medicament device 160. Parameters are software, firmware, or hardware data that control settings or specific instruction sets to be carried out by the computing architecture of the medicament device 160. Example parameters include, but are not limited to: (i) medicament dispensing reminder times, delays, or other similar settings, (ii) personalized audio ringtones for playback on an audio speaker of a medicament device, in some instances in association with particular device functions, (iii) software instructions for controlling the operation of the sensor 120 function, (iv) calibration and configuration values for sensing and output components, and (v) unique device identifiers, authentication keys, and encryption keys. Some or all of the parameters of the sensor 120 may be stored in the client 110. The client 110 communicates with the sensor 120 when parameters are updated, so that the client 110 can transmit the updated parameters for storage within and use by the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
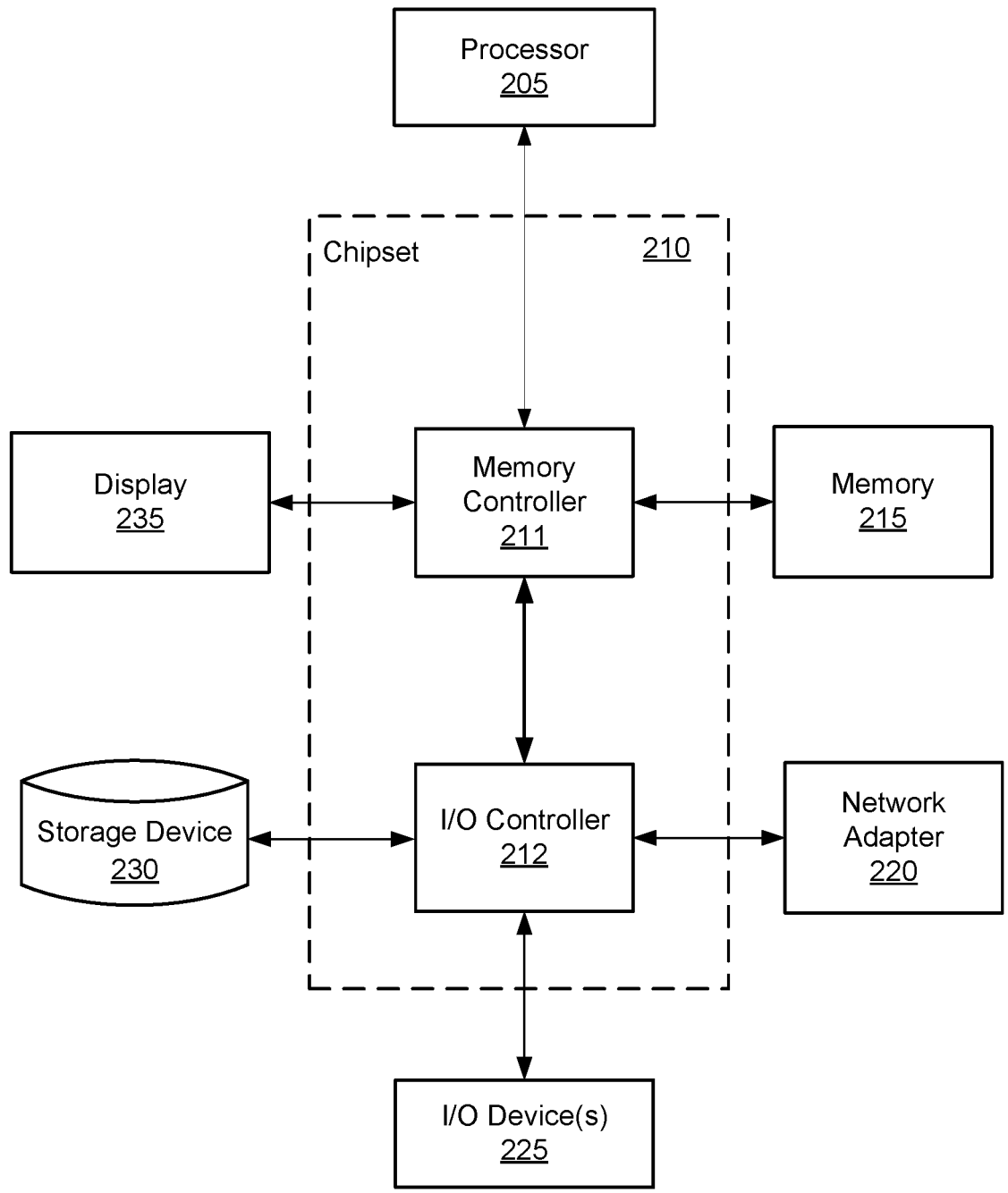
FIG. 2 is a high-level block diagram illustrating an example computing device used either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use of analytics system 100 by many different clients 110 through network 150, and thus at a high level can be generally characterized as a cloud-based system. The application server 130 generally provides a platform for patients 111 and healthcare providers 112 to report data recorded by the sensors 120 associated with their medicament devices 160 including both rescue medication and controller medication events, collaborate on medication treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identifying information about the patient such as age, gender, current rescue medication, current controller medication, notification preferences, a controller medication adherence plan, a patient's relevant medical history, and a list of non-patient users authorized to access the patient profile. The profile may further specify a device identifier, such as a unique media access control (MAC) address identifying the one or more clients 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) or by time period (e.g., weekly, monthly, yearly).

The application server 130 receives rescue medication event information from the client 110 or the sensor 120, triggering a variety of routines on the application server 130. In the example implementations described below, the data analysis module 131 executes routines to access asthma event data as well as other data including a patient's profile, analyze the data, and output the results of its analysis to both patients 111 and healthcare providers 112. This process is generally referred to as an asthma risk analysis. The asthma risk analysis may be performed at any point in time, in response to a rescue event, due to a relevant change in the patient's environment, and in response to any one of a number of triggering conditions discussed further below.

Other analyses are also possible. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that is distributed to emergency assistance providers 112. Notifications may also include the results of the asthma risk analysis performed by the data analysis module 131. More information regarding the types of notifications that may be sent and the content they may contain is further described below.

In addition to providing push notifications in response to an asthma risk analysis, notifications may also be provided as pull notifications, at particular time intervals. Additionally, some notifications (whether push or pull) may be triggered not in response to an asthma risk analysis performed in response to a rescue medication event, but instead in response to a risk analysis performed in response to one of the underlying factors in the asthma risk analysis changing, such that an updated notification is warranted. For example, if weather conditions indicate that an increase in air pollution is occurring or is imminent, this may trigger the carrying out of asthma risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma risk analyses) that incorporate data from multiple patients (e.g., aggregate rescue medication event data) and are provided to users is de-identified so that personally identifying information is removed to protect patient privacy.

The database server 140 also stores non-patient data used in asthma risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, and air quality index. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), JavaScript Object Notation (JSON) etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client 110 will vary in size, power requirements, and performance from those used in the application server 130 and the database server 140. For example, clients 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3:
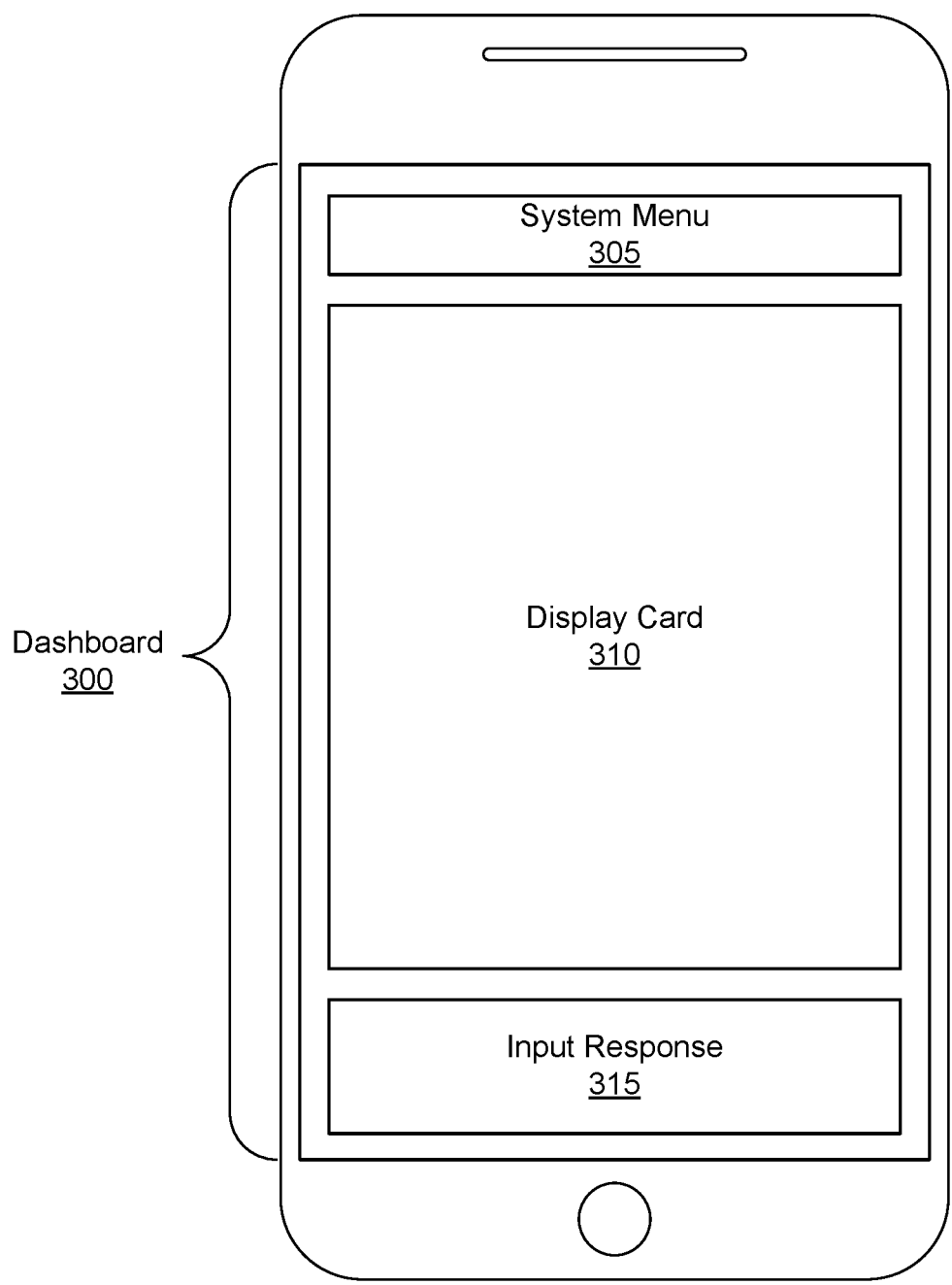
FIG. 3 is a graphical user interface of a client application that provides inputs and/or outputs from a user to an asthma analytics system, according to one embodiment.

The dashboard, for example dashboard 300 illustrated in FIG. 3, allows users to interact with the analytics system 100. The dashboard 300 provides a means to transfer information on a user-to-user (e.g., patient 111 to healthcare provider 112) or user-to-system/system-to-user basis. Dashboards 300 are accessed through the client application 115 on the client 110 and provide a mechanism for both patients and healthcare providers to monitor medication rescue events, exchange personalized patient healthcare information, and receive notifications such as rescue event risk notifications. Patients 111 may communicate with other healthcare providers 112 and other patients 111 through the dashboard 300, for example, to discuss and share information about breathing challenges, medication usage, or breathing challenge management. The ability to share healthcare information may give patients or healthcare care providers experiencing a similar issue a way to share individual perspectives.

The dashboard 300 also allows authorized healthcare providers 112 to access a list of patients to view, annotate, update, interact with, and export information about patient and community data and statistics in various demographics or geographic segments. Using the dashboard 300, healthcare providers are able to monitor patients 111 individually or in aggregate, to receive and provide feedback on how their associated patient populations are responding to breathing challenge management guidance. A healthcare provider 112 who has access to individual or multiple patients 111 has the ability to establish notification thresholds, set parameters for the notifications, and receive notifications when patients' 111 event history matches certain conditions (e.g. rescue event). Additionally, the dashboard 300 can receive and display regular reports of event patterns for specific demographics generated by the analytics system 100.

The dashboard 300 presents a variety of information including tabular data, graphical visualizations, and analyses to users through display "cards" 310. Display cards 310 are conformably suited to smaller displays typical of portable clients 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of an risk analysis. The dashboard 300 will process the notification and determine which card/s to use to present the information in the notification. Continuing the example, the recipient of the notification may make a request to pull data from the application server 130. The application server 130 provides the requested data in another notification, and the dashboard 300 then determines which display card 310 to display the requested information.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event, trend, education, and alert display cards.

Event cards include data relating to rescue medication events, such as a list of historical medication rescue events for a specific patient, or patient rescue event data overlaid on a geographical map for a specific provider.

IV. Medicament Device Sensor

Figure 4A:
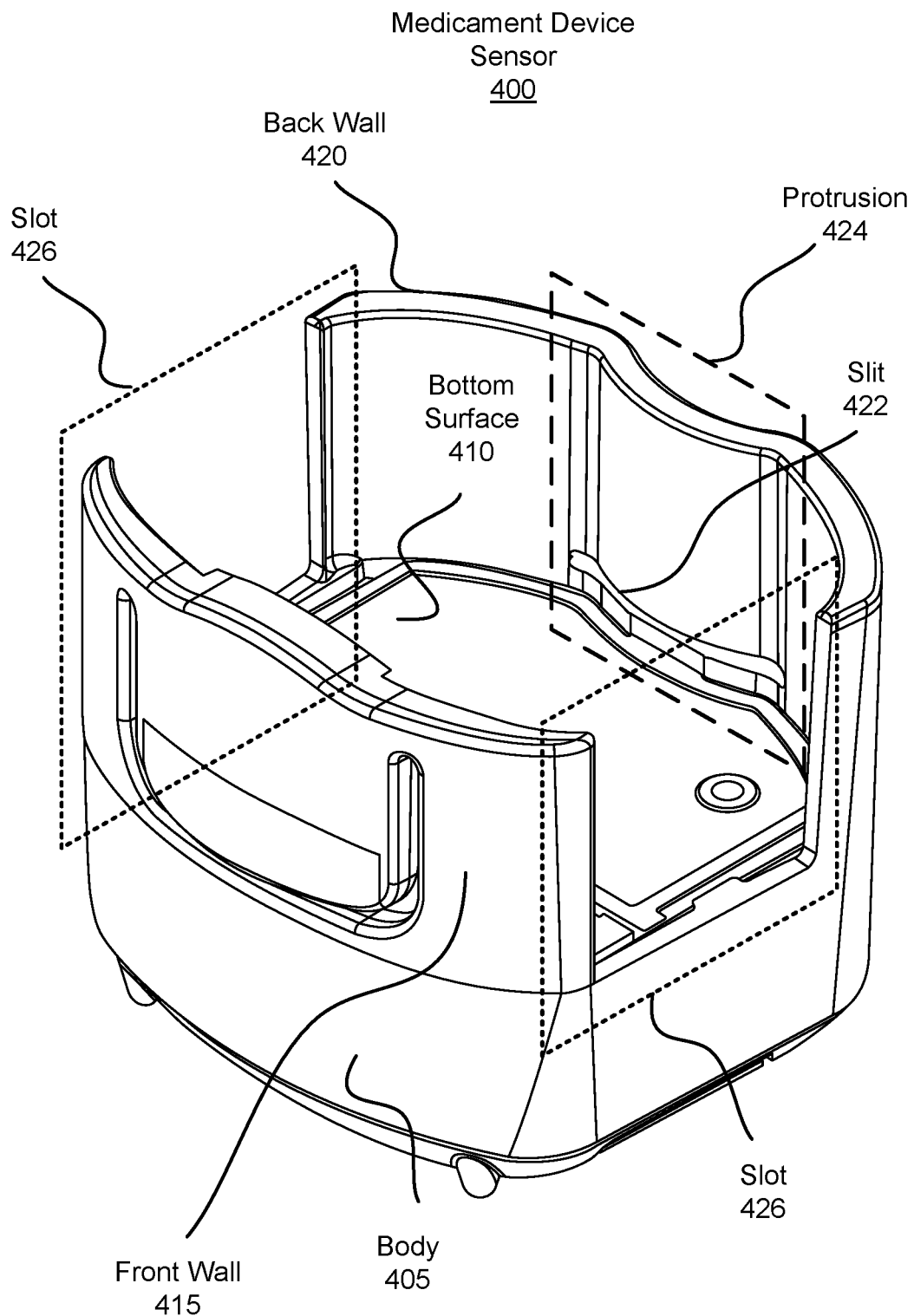
FIG. 4A is a perspective view of the medicament device sensor, according to one embodiment.
Figure 4B:
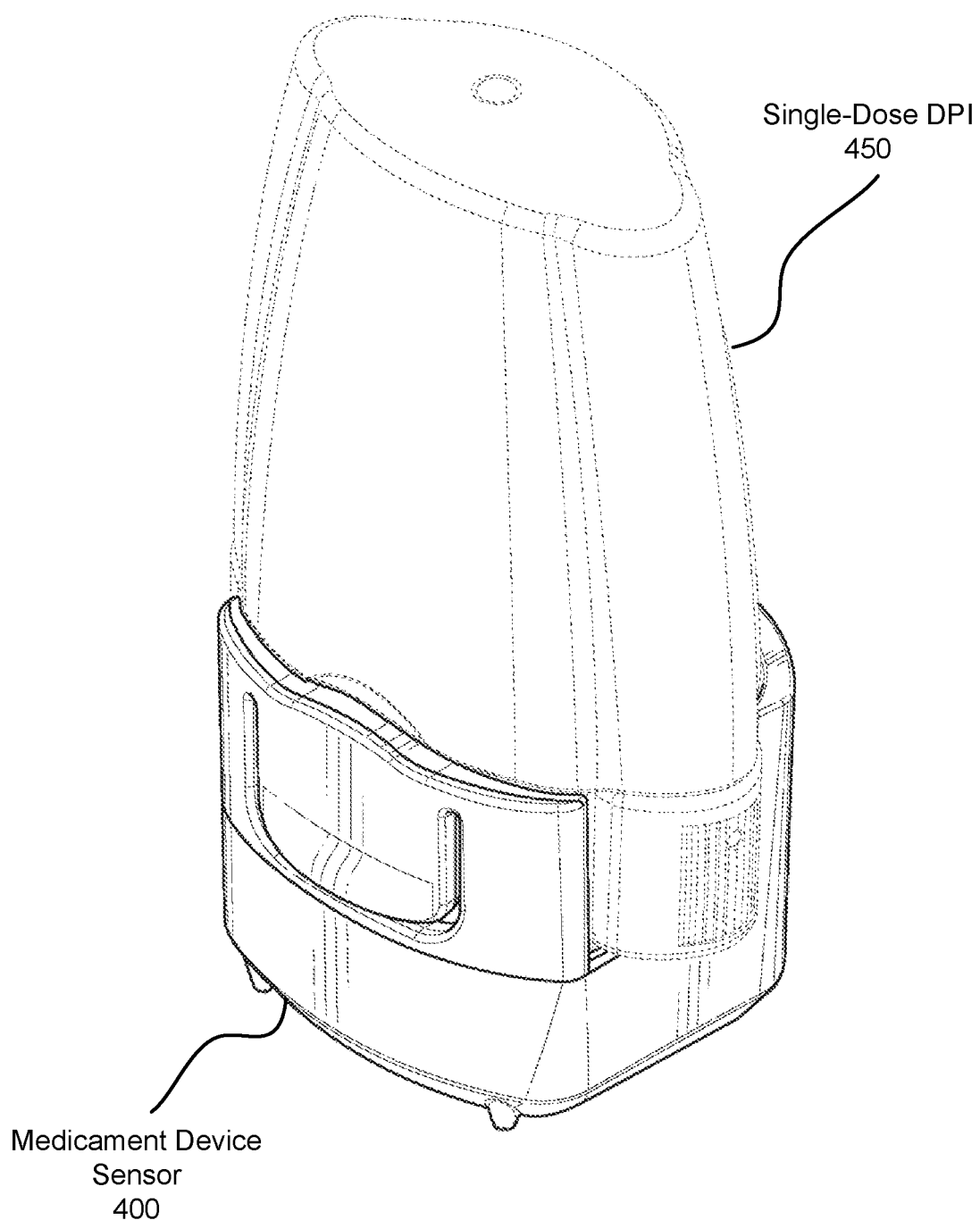
FIG. 4B is a perspective view of the medicament device sensor attached to a single dose inhaler, according to one embodiment.

FIG. 4A is a perspective view of a medicament device sensor 400, according to one embodiment. The medicament device sensor 400 is a monitoring attachment for a single-dose dry powder inhaler (DPI), where the sensor 400 includes various sensors for accurately recording an instance of medicament dispensing by the DPI. The medicament device sensor 400 comprises a body 405 and two walls—a front wall 415 and a back wall 420. The body 405 has an internal housing which can store various computing components for the monitoring attachment and a bottom surface 410 where various sensors are coupled to for monitoring use of the DPI. In various other embodiments, the medicament device sensor 400 may be coupled to other types of inhalers, not just the DPI. In these other embodiments, the same principles disclosed within this present disclosure may be applied in the embodiments of medicament device sensors coupling to other types of inhalers. FIG. 4B is a perspective view of the medicament device sensor 400 attached to a DPI 450, according to one embodiment.

The body 405, the front wall 415 and the back wall 420 are composed of a lightweight, sturdy material. Example materials include thermoplastics, thermosets, polymers, composites, or some combination thereof. The shape of the body 405 with the front wall 415 and the back wall 420 has mirror symmetry in one dimension and asymmetry in the other two dimensions. The asymmetry in at least two dimensions provides a single orientation with which the medicament device sensor 400 attaches to the medicament device 160. The front wall 415 also contains a securement clip 440 which will be further described in conjunction with FIGS. 4D & 5.

On either side of the mirror symmetry plane, the front wall 415 and the back wall 420 extend upward leaving symmetrical slots 426 on either side of the mirror symmetry plane. The slots 426 on either side are shaped and oriented so as to receive corresponding protrusions on a portion of a bottom surface of the medicament device 160. The portion of the medicament device 160 with the protrusions has matching symmetry to that of the attachment. The complementary shapes of the attachment side wall, including the bottom surface of the body 405, the front wall 415, and the back wall 420 provide the single orientation for the medicament device sensor 400 to securely attach onto the portion of the medicament device 160.

In some embodiments, the back wall 420 includes a protrusion 424 which holds the medicament device 160 in place when the medicament device sensor 400 is attached to the medicament device 160. In FIG. 4A, the back wall 420 includes a slit 422 allowing a protrusion 424 of the back wall 420 above the slit 422 to flex more easily. When the medicament device 160 is coupled to the medicament device sensor 400, the protrusion 424 of the back wall 520 contacts the medicament device 160 to hold the medicament device 160 in place. When a user applies a decoupling force on the medicament device 160 against the medicament device sensor 400, the protrusion 424 of the back wall 420 can flex outward away from the medicament device 160 allowing the medicament device 160 to be easily removed from the medicament device sensor 400. The protrusion 424 of the back wall 520 being used for securing the medicament device sensor 400 to the medicament device 160 will be further described in conjunction the discussion of the securement clip 440 in FIGS. 4D & 5.

Figure 4C:
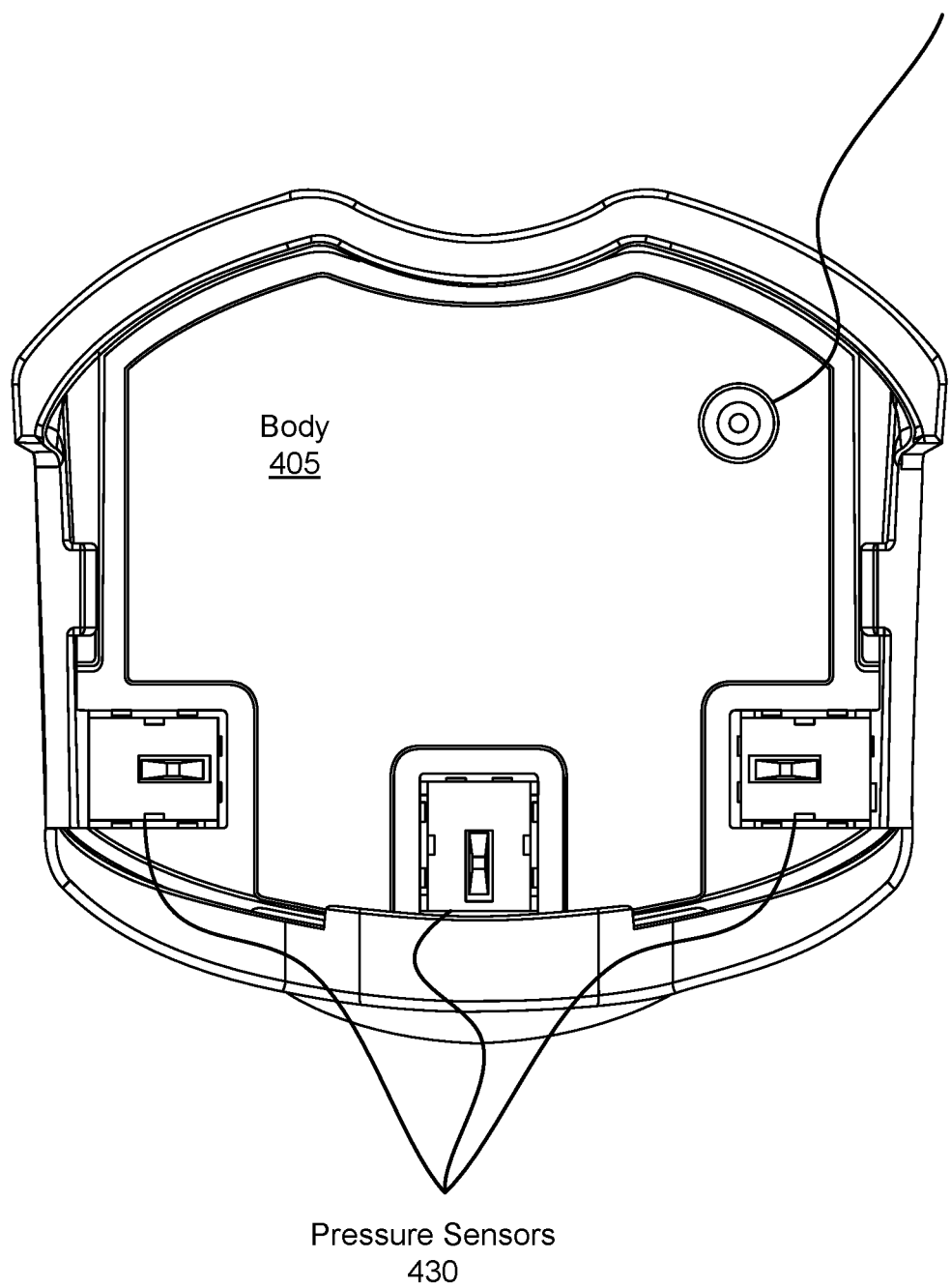
FIG. 4C is a top-plan view of the medicament device sensor, according to one embodiment.

FIG. 4C is a top-plan view of the medicament device sensor 400, according to one embodiment. The medicament device sensor 400 is configured to record and to report medicament dispensing events by the medical inhaler to which it is attached as described above in reference to I.B. MEDICAMENT DEVICE AND SENSOR. The medicament device sensor 400 includes an audio sensor 425 and multiple pressure sensors 430. Although not shown, the medicament device sensor 400 also includes a battery, a wireless transmitter and receiver (e.g., a Bluetooth transceiver), a non-transitory computer-readable storage medium, and a computer processor. These various components are placed in the internal housing of the body 405. Although this description and the example embodiments describe the medicament device sensor 400 with the above listed components, other embodiments may include additional or fewer components while maintaining the principles described herein. For example, instead of a Bluetooth transmitter and receiver, the medicament device sensor 400 could more generally contain a wireless transmitter and receiver using other mediums and/or formats of wireless communication with a remote computing device.

As introduced above, the medicament device sensor 400 comprises the body 405 with a bottom surface 410 and an internal housing. In FIG. 4C, only the bottom surface 410 is viewable. Along the bottom surface 410, the medicament device sensor 400 has at least one audio sensor 420 placed on the bottom surface 410 of the body 405 which is configured to detect audio signals corresponding to various functions of the medicament device 160 from the bottom of the medicament device 160. Multiple pressure sensors 430 placed on the bottom surface 405 of the body 405 are configured to detect pressure associated with other functions of the medicament device 160 in tandem or in sequence with the audio sensor 425.

The audio sensor 420 detects sounds corresponding to a spinning of a capsule containing medicament by the medicament device 160 prior to inhalation and sounds corresponding to inhalations during medicament dispensing events. As a user presses one or both dosing buttons on the medicament device 160, the medicament device 160 punctures a single-dose capsule of dry powder medicament. Prior to inhalation, the single-dose capsule is spun in a chamber of the medicament device 160. The audio sensor 420 records an acoustic intensity of the single-dose capsule spinning in the chamber. The detected spinning of the single-dose capsule is indicative of presence of the single-dose capsule within the medicament device 160. In addition to or in isolation of recording the spinning of the capsule containing the medicament, the audio sensor 420 records an inhalation indicative of medicament dispensing as a medicament dispensing event.

The inhalation represents confirmation of successful medicament dispensing by the medicament device 160. The audio sensor 420 can send audio files of the inhalation corresponding with medicament dispensing events to the processor. The processor, in turn, can send the audio files to a remote computing device via a wireless transmitter for analysis on the remote computing system. In other embodiments, the audio sensors 420 can be further configured to detect audio corresponding to other functions of the medicament device sensor 400.

The multiple pressure sensors 430 detects securement of the medicament device sensor 400 and activation of medicament dispensing by the medicament device 160 through detection of pressing of medicament device 160 dosing buttons that cause medicament dispensing. In some embodiments, the plurality of pressure sensors 430 comprises limit switches. The limit switches operate to detect pressure when pressed; however, the limit switches have a maximum limit as to how far the limit switches press. Once any depression is sensed, the limit switch signals the detection of depression.

Of the multiple of pressure sensors 430, there is a center pressure sensor arranged on the bottom surface 410 of the body 405 of the medicament device sensor 400 so as to cause the bottom surface of the medicament device 160 to press the center pressure sensor. As the medicament device 160 presses the center pressure sensor, the center pressure sensor detects attachment of the medicament device sensor 400 to the medicament device. The depression of the center pressure sensor can then be reported to the processor as confirmation of secure attachment.

There are also two pressure sensors of the plurality of pressure sensors 430 which are coupled to dosing buttons on the medicament device 160, and are aligned underneath the medicament dosing buttons of the medicament device 160. Each pressure sensor corresponds to one dosing button to detect depression of that button. When one or both of the dosing buttons are depressed by a patient, the medicament device 160 pierces the single-dose capsule thus priming the medicament for dispensing by the medicament device 160. The two pressure sensors confirm pressing of the dosing buttons thereby indicating priming of the medicament.

The processor coordinates recording and activation of the audio sensor 420 and the plurality of pressures sensors 430. When one pressure sensor detects attachment of the medicament device sensor 400 to the medicament device 160, the processor can activate the audio sensor 420, remaining pressure sensors of the plurality of pressure sensors 430, the GPS receiver, the Bluetooth transmitter and receiver, or some combination thereof. The processor may notify a client 110 a confirmation of secure attachment of the medicament device sensor 400 to the medicament device 160 as detected by the center pressure sensor. The processor can receive confirmation from the two or more pressure sensors configured to detect depression of the medicament device 160 dosing buttons. Then the processor can activate the audio sensor 420 for audio confirmation of an inhalation associated with the dispensing of medicament by the medicament device 160. Alternately, the processor can record a medicament dispensing event if one or more pressure sensors indicates depression of limit switches and an inhalation is confirmed by the audio sensor 420.

The processor may additionally record with each medicament dispensing event a time of the event and may also record geographical location coordinates as received by a GPS receiver or other similar component (implemented in software, hardware, or firmware). The processor stores these medicament dispensing events as event records on the computer-readable storage medium. Then the processor activates the Bluetooth transmitter and receiver so as to communicate event records from the computer-readable storage medium to the client 110

Figure 4D:
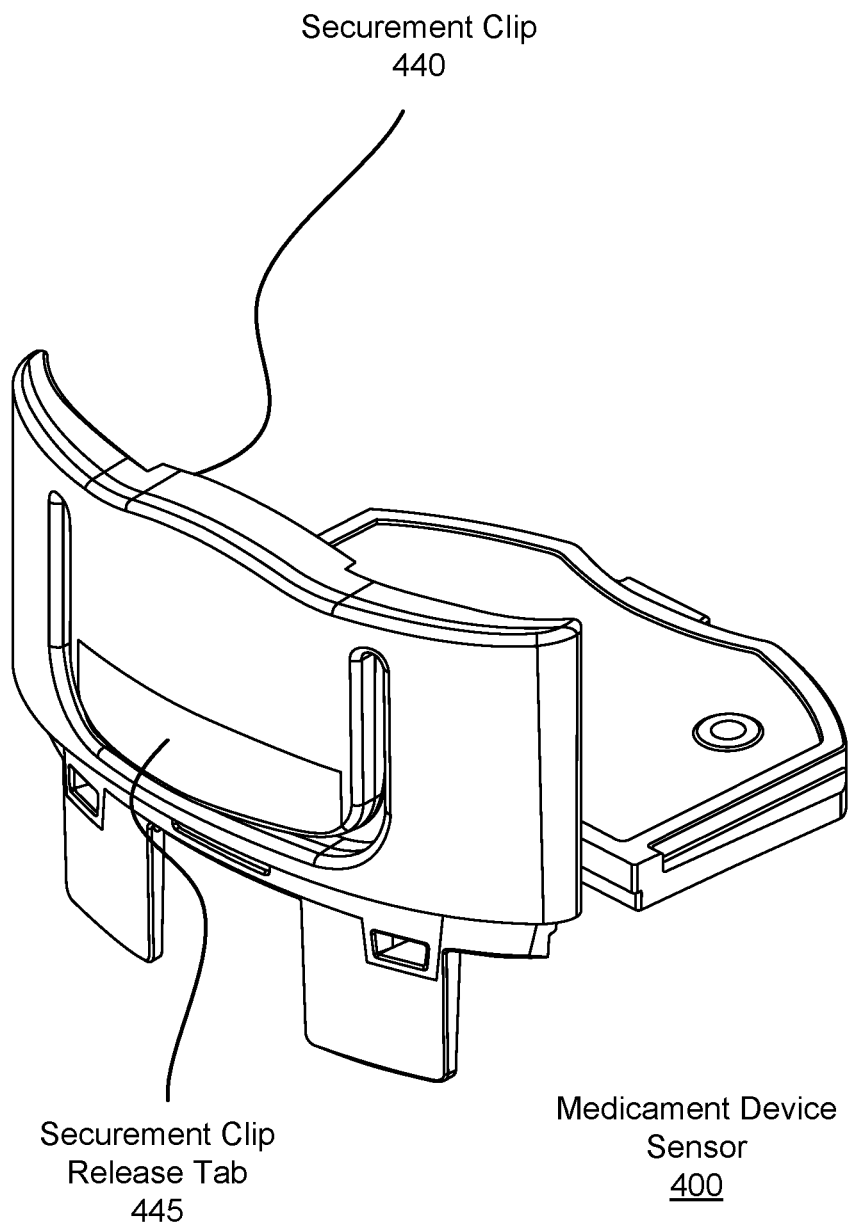
FIG. 4D is a perspective view of a portion of the medicament device sensor with the securement clip, according to one embodiment.
Figure 4E:
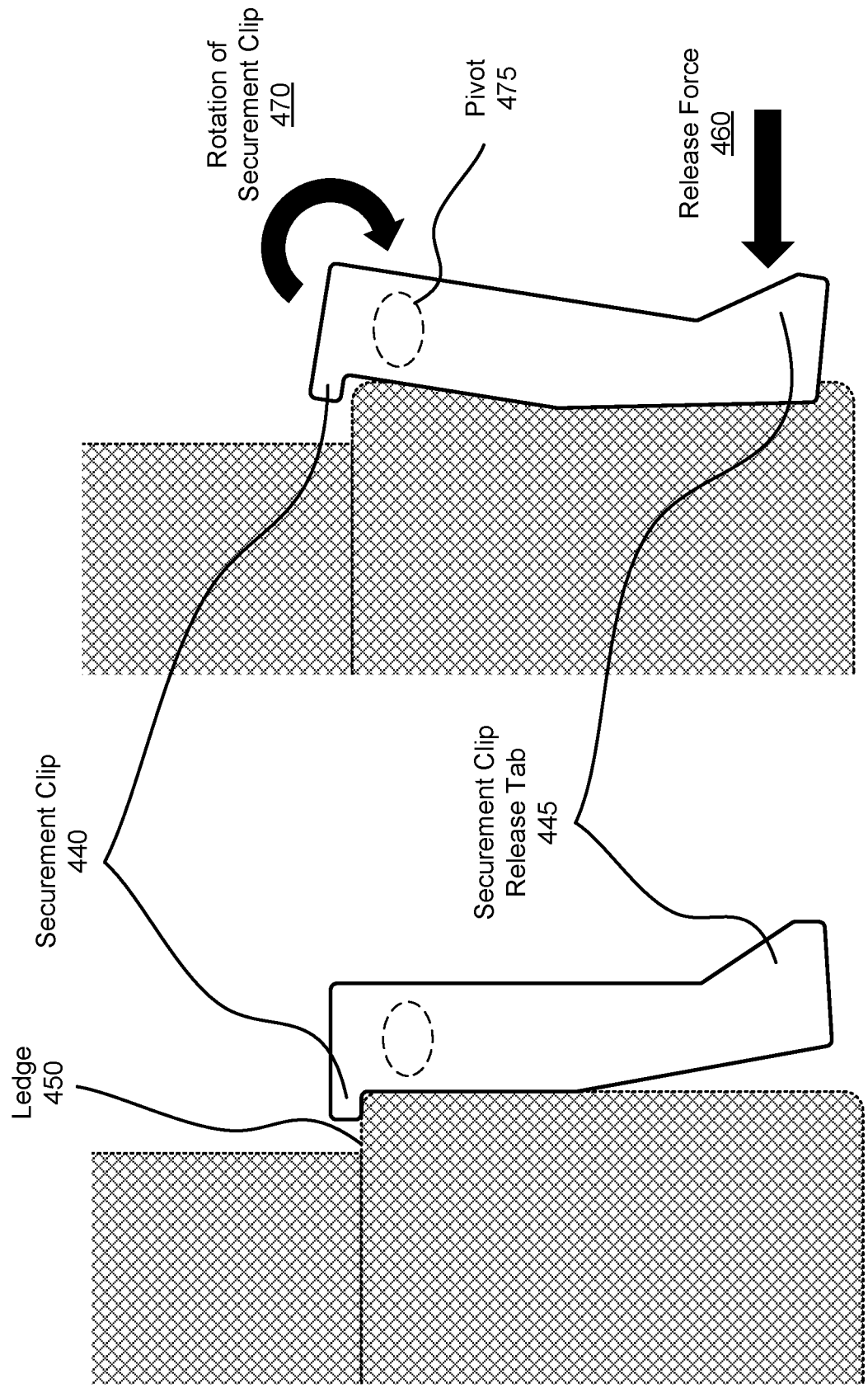
FIG. 4E is a cross-sectional representation of a portion of the securement clip next to the single dose inhaler, according to one embodiment.

FIG. 4D is a perspective view of a portion of the medicament device sensor 400 with the securement clip 440; FIG. 4E is a cross sectional view of the securement clip 440. The securement clip 440 is placed on the front wall 415 of the medicament device sensor 400 and clips over a ledge 450 on the medicament device 160 shown in FIG. 4E. When the medicament device sensor 400 slides onto the medicament device 160 in the one orientation due to restriction by the front wall 415 and the back wall 420, the securement clip 440 bends around the medicament device 160 until it clips on the ledge 450 of the medicament device 160. When the securement clip 440 is clipped onto the ledge 450 of the medicament device 160, the medicament device sensor 400 is securely attached to the medicament device 160. Additionally, the protrusion on the back wall 420 as shown in FIG. 4A is in contact with the medicament device 160 so as to ensure that the ledge 450 is pressed against the front wall 415 with the securement clip 440.

To detach the medicament device sensor 400, there is a securement clip release tab 445 which aids in bending the securement clip 440 away from the ledge 450 of the medicament device 160. When a release force 460 is applied on the securement clip release tab 445, there is a rotation 470 of securement clip 440 around a pivot point 475 denoted by the dashed oval in FIG. 4E. The rotation 470 bends the securement clip 440 away from the ledge 450 of the medicament device 160 such that the medicament device sensor 400 may slide out from the medicament device 160. In the illustration of FIG. 4E, once the securement clip 440 bends away from the ledge 450, the medicament device 160 can slide vertically relative to the medicament device sensor 400. With one securement clip 440 and one corresponding ledge on the medicament device 160, the securement clip 440 insures attachment of the medicament device sensor 400 in the proper orientation.

In additional embodiments, the positioning of the securement clip 440 can vary along the front wall 415. Similarly in alternate embodiments, the dimensions of the securement clip 440 can vary so as to provide a longer clip for clipping on the ledge 450 of the medicament device 160. In some embodiment, the securement clip 440 is composed of a durable and flexible material. The flexibility of the securement clip 440 provides the ability of the securement clip 440 to bend around the ledge 450. The durability of the securement clip 440 insures that the securement clip 440 doesn't deform when the release force 460 is applied to the securement clip release tab 445.

V. Additional Considerations

Although the discussion above focuses on asthma specifically, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A medicament device sensor configured for removable attachment to a medicament device comprising:
   a body comprising a bottom surface, the bottom surface shaped so as to mate to a corresponding outer surface of the medicament device;
   a first wall perpendicular to the bottom surface coupled to a first edge of the bottom surface, comprising a securement clip configured to attach the first wall of the medicament device sensor to a ledge on a complementary surface of the medicament device in a fixed orientation, wherein the securement clip comprises a release tab that when pressed causes the securement clip to rotate away from the ledge such that the medicament device can slide vertically relative to the medicament device sensor, wherein a topmost surface of the release tab is contiguous with a topmost surface of the first wall;
   a second wall perpendicular to the bottom surface coupled to a second edge of the bottom surface, the second edge opposite that of the first edge;
   an audio sensor coupled to the bottom surface of the body configured to detect audio corresponding to use of the medicament device, wherein the audio sensor records an acoustic intensity of a capsule spinning within the medicament device; and
   a plurality of pressure sensors coupled to the bottom surface of the body configured to detect pressure corresponding to use of the medicament device.

2. The medicament device sensor of claim 1, wherein the second wall comprises a protrusion configured to come in contact with the medicament device when the medicament device sensor is attached to the medicament device.

3. The medicament device sensor of claim 1, wherein the first wall and the second wall has mirror symmetry in one dimension and asymmetry in at least two dimensions such that the medicament device sensor couples to the medicament device in a fixed orientation.

4. The medicament device sensor of claim 1, wherein the audio sensor is configured to detect an inhalation corresponding to dispensing of medicament by the medicament device.

5. The medicament device sensor of claim 1, wherein the audio sensor is further configured to detect a sound corresponding to motion of a capsule containing medicament within the medicament device.

6. The medicament device sensor of claim 1, wherein each pressure sensor of the plurality of pressure sensors comprises a limit switch.

7. The medicament device sensor of claim 1, wherein one of the plurality of pressure sensors is positioned on the bottom surface so as to detect pressure from the medicament device when coupled to the medicament device sensor corresponding to secure attachment of the medicament device sensor to the medicament device.

8. The medicament device sensor of claim 1, wherein at least one of the plurality of pressure sensors is positioned on the bottom surface so as to detect pressure from depression of a dosing button of the medicament device corresponding to priming of the medicament device.

9. The medicament device sensor of claim 1, wherein the medicament device sensor further comprises:
   a computer-readable storage medium coupled to the body; and
   a processor coupled to the body configured to process audio data from the audio sensor and pressure data from the plurality of pressure sensors on the computer-readable storage medium.

10. The medicament device sensor of claim 9 further comprising:
    a GPS receiver coupled to the body configured to receive location data and time data.

11. The medicament device sensor of claim 9 further comprising:
    a wireless transmitter coupled to the body configured to transmit data through wireless frequencies.

12. A medicament system comprising:
    a medicament device configured to dispense a rescue medication to a patient; and
    a medicament device sensor configured for removable attachment to the medicament device comprising:
       a body comprising a bottom surface, the bottom surface shaped so as to mate to a corresponding outer surface of the medicament device;
       a first wall perpendicular to the bottom surface coupled to a first edge of the bottom surface, comprising a securement clip configured to attach the first wall of the medicament device sensor to a ledge on a complementary surface of the medicament device in a fixed orientation, wherein the securement clip comprises a release tab that when pressed causes the securement clip to rotate away from the ledge such that the medicament device can slide vertically relative to the medicament device sensor, wherein a topmost surface of the release tab is contiguous with a topmost surface of the first wall;
       a second wall perpendicular to the bottom surface coupled to a second edge of the bottom surface, the second edge opposite that of the first edge;
       an audio sensor coupled to the bottom surface of the body configured to detect audio corresponding to use of the medicament device, wherein the audio sensor records an acoustic intensity of a capsule spinning within the medicament device; and
       a plurality of pressure sensors coupled to the bottom surface of the body configured to detect pressure corresponding to use of the medicament device.

13. The medicament system of claim 12, wherein the second wall comprises a protrusion configured to come in contact with the medicament device when the medicament device sensor is attached to the medicament device.

14. The medicament system of claim 12, wherein the audio sensor is configured to detect one or more of:
    an inhalation corresponding to dispensing of medicament by the medicament device; and
    a sound corresponding to motion of a capsule containing medicament within the medicament device.

15. The medicament system of claim 12, wherein one of the plurality of pressure sensors is positioned on the bottom surface so as to detect pressure from the medicament device when coupled to the medicament device sensor corresponding to secure attachment of the medicament device sensor to the medicament device.

16. The medicament system of claim 12, wherein the medicament device sensor further comprises:
    a computer-readable storage medium coupled to the body; and a processor coupled to the body configured to process audio data from the audio sensor and pressure data from the plurality of pressure sensors on the computer-readable storage medium.

17. A medicament system comprising:
a medicament device configured to dispense a rescue medication to a patient, the medicament device comprising:
    a computer-readable storage medium; and
    a processor configured to process audio data from audio sensors and pressure data from pressure sensors on the computer-readable storage medium; and
a medicament device sensor configured for removable attachment to the medicament device comprising:
    a body comprising a bottom surface, the bottom surface shaped so as to mate to a corresponding outer surface of the medicament device;
    a first wall perpendicular to the bottom surface coupled to a first edge of the bottom surface, comprising a securement clip configured to attach the first wall of the medicament device sensor to a ledge on a complementary surface of the medicament device in a fixed orientation, wherein the securement clip comprises a release tab that when pressed causes the securement clip to rotate away from the ledge such that the medicament device can slide vertically relative to the medicament device sensor, wherein a topmost surface of the release tab is contiguous with a topmost surface of the first wall;
    a second wall perpendicular to the bottom surface coupled to a second edge of the bottom surface, the second edge opposite that of the first edge;
    an audio sensor coupled to the bottom surface of the body configured to detect audio corresponding to use of the medicament device, wherein the audio sensor records an acoustic intensity of a capsule spinning within the medicament device; and
    a plurality of pressure sensors coupled to the bottom surface of the body configured to detect pressure corresponding to use of the medicament device.

18. The medicament system of claim 17, wherein the second wall comprises a protrusion configured to come in contact with the medicament device when the medicament device sensor is attached to the medicament device.

19. The medicament system of claim 17, wherein the audio sensor is configured to detect one or more of:
    an inhalation corresponding to dispensing of medicament by the medicament device; and
    a sound corresponding to motion of a capsule containing medicament within the medicament device.

20. The medicament system of claim 17, wherein one of the plurality of pressure sensors is positioned on the bottom surface so as to detect pressure from the medicament device when coupled to the medicament device sensor corresponding to secure attachment of the medicament device sensor to the medicament device.

* * * * *